US00PP10147P

United States Patent [19]

Probasco

[11] Patent Number: Plant 10,147

[45] Date of Patent: Dec. 9, 1997

[54] HOP PLANT NAMED 'H900322-4'

[75] Inventor: Gene Probasco, Yakima, Wash.

[73] Assignee: John I. Haas, Inc., Yakima, Wash.

[21] Appl. No.: 608,090

[22] Filed: Feb. 28, 1996

[51] Int. Cl.[6] ..... A01H 5/00

[52] U.S. Cl. ..... Plt./100

[58] Field of Search ..... Plt./100

[56] References Cited

U.S. PATENT DOCUMENTS

P.P. 9,511 4/1996 Tanikoshi et al. ..... Plt./100

*Primary Examiner*—James R. Feyrer

[57] ABSTRACT

A new and distinct triploid hop, *Humulus lupulus*, plant selected from the progeny of USDA '21055' X John I. Haas, Inc. No. '833-53M', characterized by an unusually high percentage of alpha-acids, coupled with a high yield. This plant also has a high amount of farnesene as a component in the essential oil (8.8% of the total oil is farnesene). None of the USA high alpha-acids varieties has farnesene in the oil. Further, 'H900322-4' (hereinafter "H900322-4") has a higher cohumulone content (44.0%) of the alpha-acids than any of the USA high alpha-acids varieties. Harvest maturity is medium-late, with 'Nugget' and following 'Galena' by about 1 week. Cone size is medium to large yet compact and ovoid, and easily machancially harvested. Cones are non-shattering, and have bracts that are of a darker green color than bracteoles, resulting in a striped appearance.

3 Drawing Sheets

BACKGROUND AND SUMMARY OF INVENTION

Hops are grown commercially for use in flavoring beers, stouts and ales. Lupulin glands found inside female hop cones provide the resins and essential oils which are the primary components of the hop flavor each variety imparts to beers, stouts and ales. New hop varieties are evaluated for their growing characteristics, per acre hop cone yields (dried to approximately 8% moisture), the chemical composition of the resins and essential oils contained within the hop cone's lupulin glands, and the unique flavor each variety imparts to beers, stouts and ales. Only female hop plants produce cones containing lupulin glands, and thus only female hop plants have any commercial value. Male hop plants have no commercial value other than for use in breeding programs to create new varieties.

This invention relates to a new and distinct variety of hop and more particularly to an asexually reproduced hop variety selected from among hop plants resulting from a controlled cross pollination between an unpatented tetraploid USDA 21055 (non commercial breeding line) female hop plant with unpatented John I. Haas, Inc. (Haas) male hop plant No. 833-53M.

Haas male hop plant No. 833-53M originated from a controlled cross pollination in 1982 between unpatented female hop plant USDA Accession No. 21055 and unpatented male hop plant USDA Accession No. 63015M.

The controlled cross pollination program resulting in the creation of the new hop variety, hereafter called H900322-4 was performed in 1989 by Mr. Gene Probasco, a botanist employed by John I. Haas, Inc., in a Haas greenhouse located at 1112 North 16th Avenue, Yakima, Wash., 98902. Mr. Probasco discovered the H900322-4 variety in 1991 among the hop plants which were produced from the seeds resulting from the above described controlled cross pollination program.

The seeds from the cross between tetraploid USDA 21055 female hop plant and Haas male hop plant No. 833-53M were planted in a Haas greenhouse in 1990. The most vigorous plants resulting from the cross were selected and planted in a Haas hop field located at Wada Farm, Yakima Golding Farms, Toppenish, Wash. This planting did not produce a crop during the planting year.

In 1991, as a result of chemical analysis and field observations of the hop plants resulting from the tetraploid USDA 21055 female X Haas male 833-53M cross, Mr. Probasco was attracted to the H900322-4 hop plant for its unusually high percentage of alpha-acids, coupled with a reasonable projected per acre cone yield. The per acre cone yield projections were based upon the cone production of the single H900322-4 hop plant observed in 1991. The H900322-4 plant was not asexually reproduced in 1991. In 1992, the H900322-4 plant was observed again in the same location and production of alpha-acids was again high.

In 1993, second (2nd) generation rootstock from the H900322-4 variety was planted in a one acre test plot located at Home Farm, Yakima Golding Farm, Toppenish, Wash. This greenhouse produced planting did not produce a crop during the planting year.

However, in 1994 chemical analysis and field observations of the first harvestable crop of the second (2nd) generation plants in the one acre test plot provided additional information supporting the per acre cone yield and alpha-acids projections made from the original H900322-4 plant selected in 1991; confirmed the unusually high alpha-acids percentage characteristics of the new variety; and initiated the accumulation of historical agronomic data on the new variety. It is important to note that first year per acre cone yields in Washington State typically are lower than normal per acre yields for Washington State hop fields in subsequent years. Consequently, the per acre cone yield observations made from this first year one acre test plot were used to merely project anticipated normal yields for the new variety.

Also in 1994, John I. Haas, Inc., performed the first year trials of hexane extraction of the alpha-acids on bales of the H900322-4 hop variety from the first crop produced from the one acre test plot. These initial extraction trials were successful because Haas was able to extract a minimum of 93% of the alpha-acids present in the H900322-4 hop cones. John I. Haas, Inc. requires that a minimum of 93% of alpha-acids be extractable from a new hop variety in order for the new variety to be considered for potential commercial use.

In 1994, second (2nd) and third (3rd) generation rootstock from the H900322-4 variety was planted in a larger test plot of approximately 35 acres (large acreage test plot) at one of John I. Haas, Inc.'s hop farms located at Mabton, Wash. This planting did not yield a crop in 1994.

In 1995, the one acre test plot of second (2nd) generation plants at the Home Farm produced a second crop of hop cones. The second year per acre cone production was approximately three thousand pounds per acre. This is well within the range of per acre cone production for a commercially viable hop variety. The analytical data from chemical analysis of multiple random samples from bales of cones harvested from the one acre test plot showed an average alpha-acids percentage of 17.0% (ASBC spectrophotometric method). This is an unusually high alpha-acids percentage, and combined with the high yield is the primary novel characteristic of this new variety.

Also, in 1995, the large acreage test plot of second (2nd) and third (3rd) generation plants produced its first crop of hop cones. The analytical data from chemical analysis of multiple random samples from bales of cones harvested from the large acreage test plot in 1995 showed an average alpha-acids percentage of 16.8%. Field observations showed hop cone yields of two thousand eight hundred and eighty (2880) pounds per acre. This first year yield for hop cones in a large acreage test plot in Washington State were well within acceptable range for a commercially viable variety.

In 1995, John I. Haas, Inc., also performed the second year trials of hexane extraction of the alpha-acids on bales of the H900322-4 hop variety from the second crop produced from the one acre test plot. These extraction trials confirmed that Haas was again able to extract a minimum of 93% of the alpha-acids present in the H900322-4 hop cones.

All of the testing and evaluation of the H900322-4 variety's growing characteristics, per acre hop cone yield, analytical data and alpha-acids extraction tests were carried out on hop farms, laboratory facilities, and industrial extraction facilities which are wholly owned and controlled by John I. Haas, Inc.

No brewing for any beers, stouts or ales had been conducted on this new variety as of the end of the 1995 growing season.

Based upon the field observations performed, and chemical analytical data collected during this testing and evaluation program from 1991 through 1995, it appears that second (2nd) and third (3rd) generation H900322-4 hop plants demonstrate genetic stability with respect to the new variety's novel characteristic of unusually high alpha-acids yields. Also, the new H900322-4 variety demonstrates genetic stability with respect to the production of commercially viable per acre hop cone yields.

Harvest dates of the variety H900322-4 are medium-late, usually ready to pick approximately one week later than Galena and about the same time as Nugget in the Toppenish area. The compact and ovoid shape cones of this variety are mid to large in size and this aids in the ease of picking and cleaning. Adaptation to mechanical harvesting is very good, the cones detach easily from stems, leaves do not develop in the cones and the plant has a high cone to foliage ratio of 38-42% compared to 30-34% for Chinook, Galena and Nugget. The cones do not shatter during harvest.

This new hop variety has been carefully compared to its female parent, the unpatented USDA noncommercial breeding line 21055. The hop industry does not make or rely on any comparisons between new varieties and their male parents because male hops plants have no commercial value. The primary difference between the new H900322-4 variety and its female parent is the unusually high alpha-acids percentages in bales of harvested hop cones and the unusually high production of hop cones per acre.

THE DRAWINGS

The accompanying photographs illustrate the cones of the new H900322-4 variety.:

DESCRIPTION OF THE VARIETY

Figure 1:
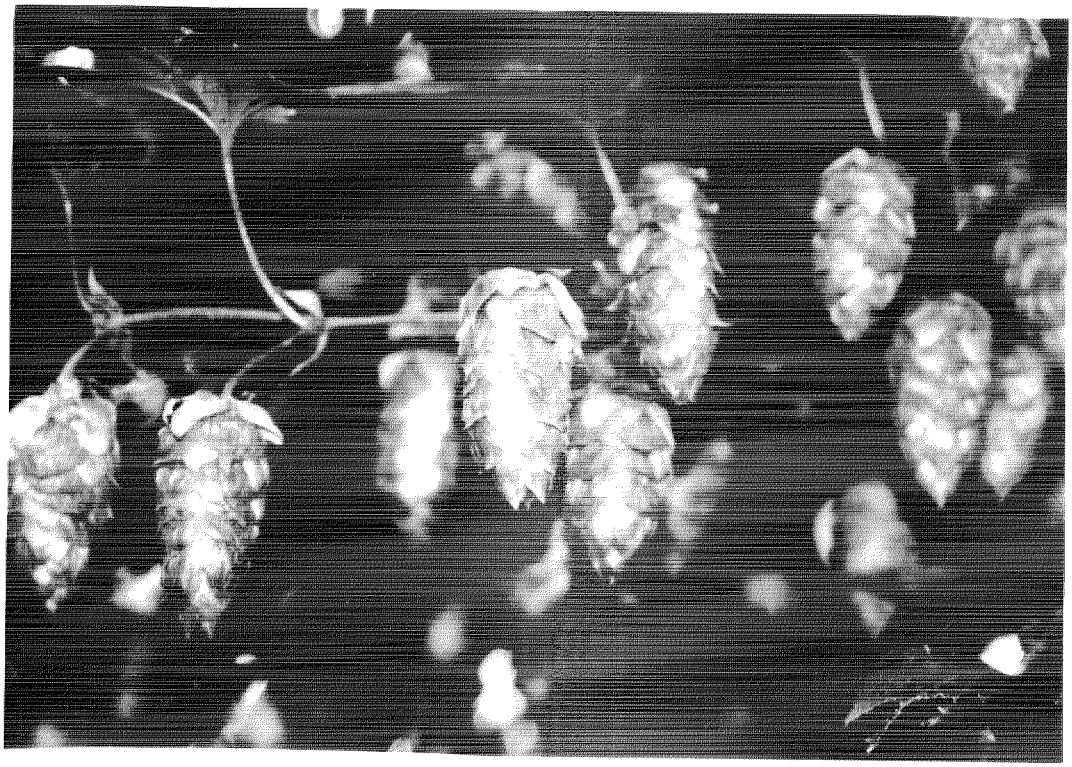
Figure 1 illustrates a close up of the cones attached to the plant.
Figure 2:
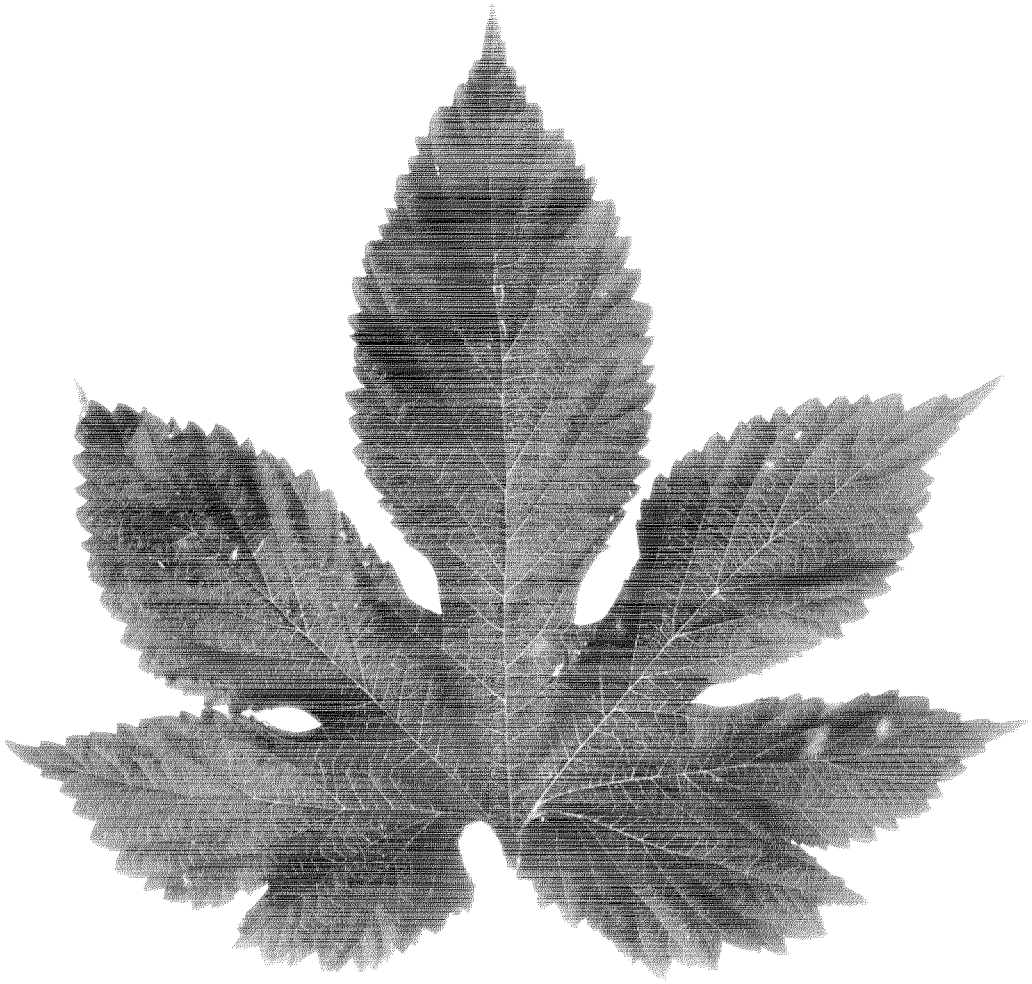
Figure 2 illustrates the leaf close up.
Figure 3:
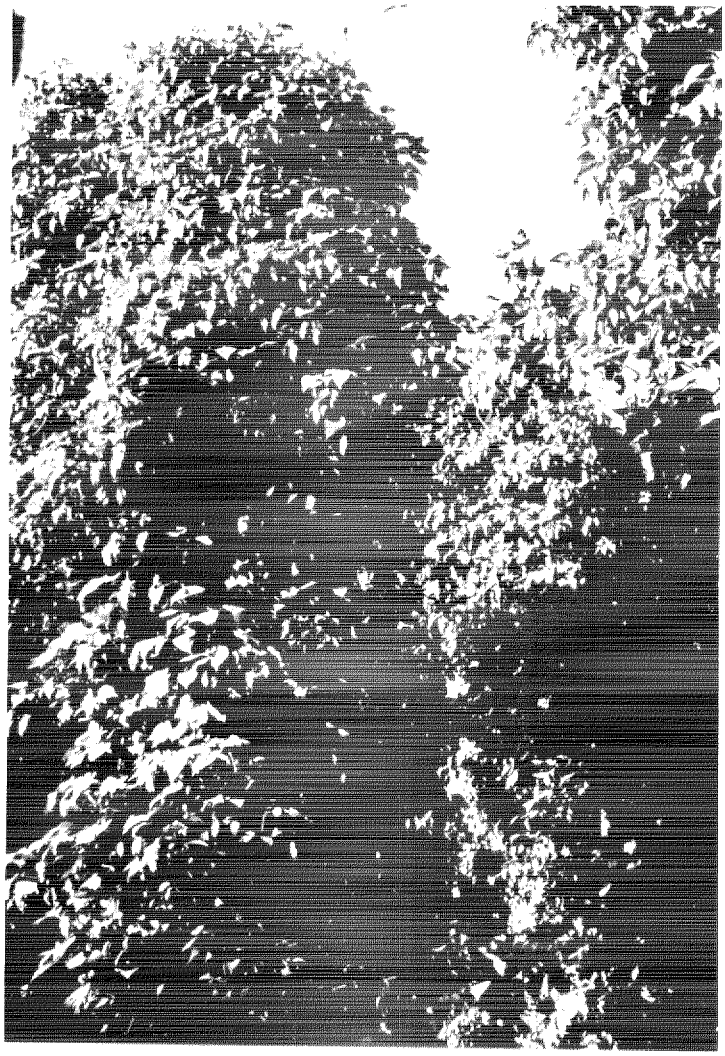
Figure 3 illustrates the appearance of the plants as they are growing in the field and approaching harvest time.

This description contains information about all botanical and analytical chemical characteristics upon which the hop industry relies in identifying and distinguishing specific hop varieties. The analytical data used to describe this new variety are subject to some variation among different samples of this new variety, due to the maturity of the hop cones sampled, climatic and growing conditions, geography, and other variables. For these reasons the analytical values used to describe this new variety are expressed in terms of ranges or averages of values rather than absolute or fixed values.

GENERAL DESCRIPTIVE INFORMATION

I. Introduction

The hop plant, *Humulus lupulus L.*, is a perennial plant which produces annual climbing bines and a perennial crown. In the Spring, the buds which have developed on the crown send out numerous shoots. The annual shoots are referred to as bines or vines and can grow up to 25 feet in a single growing season. These bines climb in a clockwise direction without the aid of tendrils, but rather with the aid of hooked hairs known as tricomes. The bine of a mature hop may be one half to three quarters of an inch thick at the six foot height. Laterals grow from the axillary buds at each node along the main bine. The inflorescenses develop from the axils of the laterals and each inflorescense becomes a single hop cone at maturity.

II. Roots

The hop crown will become woody with age, developing heavy, rough bark after the first year. Much of the hop crown consists of branched stem tissue which lies buried at a shallow depth below the surface of the soil. This stem tissue, or rhizome, produces buds which in the Spring develop into a mass of heterophyllous shoots. The crown also produces two types of roots; horizontal and vertical. The horizontal roots are fibrous, absorptive roots used for water uptake. The vertical roots, which develop from the horizontal roots, are thick and fleshy and serve as carbohydrate storage organs.

III. Stems

The annual stems grow from the crown in early Spring and twine around suitable support. Shoots of H900322-4 emerge from Winter dormancy about the same time as the commercial variety Galena which is approximately the last week of March or first week of April in the State of Washington. Initial growth rate is slightly above average, but after Spring pruning growth becomes average, which is slow compared to Galena. The stems are hexagonal in shape with the corners of the hexagon often protruding. The main stem color is green and has a dark green or purple stripe. On all sides of the stem are hairs, consisting mostly of silicates, and as these harden they become one or two sided hooks. Generally, the size of the stem at the six foot height is between ⅜ to ½ in diameter The first training for the variety H900322-4 is ideally the middle days of May. "Training"of the vines is a term used by growers which means placement of vines on a support, which has one end attached on the 18' high trellis wire and the other end secured into the soil. During training, the vines are placed on the support in a clockwise manner which is the natural helical growth pattern of all hop varieties. H900322-4 has good vigor and can reach the top of the trellis in 5–6 weeks after training.

IV. Leaves

Leaves of H900322-4 are borne in pairs at each node on the main bine and the majority of these leaves are opposite in arrangement. Located at the petiole base of each leaf is a stipule which is interpetiolar in arrangement. The bine leaves are cordate in shape with 3 to 7 palmate lobes, but mainly 7 lobes and has palmate venation. The outer two lobes of a 7 lobe leaf are commonly minor, having shallowly cut sinus clefts. The main center lobe may have a singly distinct deeply incised cleft approximately half way down each side of the lobe, but this occurs infrequently. The sinus cleft are deeply cut with leaf margins being smooth. The remainder of the leaf margins are serrate to dentate. Leaf color is green on the upper surface and lighter green on the lower surface. Stiff fine hairs on the upper surface of the leaf produce a dull appearance and rough texture. The lower surface bears many disc-shaped yellowish resin glands. The leaves are petiolate and the petioles are slightly channeled, therefore having a flat surface on the upper side. The leaf petiole extends from the main vine in a reflexed position.

V. Laterals

The laterals, or sidearms as they are often called, originate from buds in the axils of leaves of the main bine. The lateral position is "caulous" which means it grows more or less evenly spaced along the main bine.

VI. Cones

The inflorescences of H900322-4 begin to appear in late June and mature during the third week of September. As they mature, they form a conelike structure, or strobile, referred to as a "cone". These inflorescences develop on a cranked axis and the cones form in pairs or clusters. The cones develop on the laterals from the top of the plant to approximately 40 inches above the ground. The cone consists of a central rachis or strig which bears numerous bracts and bracteoles. At the base of each bracteole is an ovary which if fertilized by pollination, results in the lengthening and thickening of the central strig. Plants of this variety cannot be fertilized because the genetic make up is triploid.

The aroma of hop cones of any variety is not measurable and therefore, highly subjective. Aroma descriptions are not useful because of this subjectivity. However, the intensity of hop aroma is less debatable and for this variety could be described as medium to strong.

The hop cone of H900322-4 is ovoid to conic in shape and is tight when referring to its compactness. The tip of the cone is mostly pointed. The bract tip shape is cuspidate to almost mucronate, while the bracteole is acute to narrowly rounded. The central rachis or strig is thick compared to the strig of the variety Cluster. The cone and more specifically the bracteoles, contain numerous lupulin glands. As the hop cone matures, the lupulin glands fill and form a globular shape and are golden yellow in color. One of the most important components of these resins is the alpha-acids which gives beer its bitterness, but other components of the lupulin glands also contribute to the flavor of the beer.

The cone numbers, size and weight are direct factors in determining the yield of this variety, as well as any other variety. Climatic fluctuations, as well as cultural practices, soil type and fertility all have effects on yield. Cone uniformity with regard to size, weight, and level of maturity varies with the growing season. Cone shape is fairly uniform in the H900322-4 variety.

The hop cones of H900322-4 variety are well adapted to mechanical harvest because of their compactness and ovoid shape. The cones do not shatter during harvest.

VII. Growth Characteristics

Growth of the annual stem is rapid during a relatively short thirty-five day period during which the bine will grow approximately 20-24 feet in length. The extent of this rapid growth is very dependent on temperature, soil conditions and cultural practices.

VIII. Variability of Botanical Characteristics

The dimensions of the various components of a hop plant, including stems, cones, leaves, laterals, and internodes vary tremendously from one year to the next, from one field to the next within the same year; and even from one plant to the next within the same field. Because of the variability of climate, temperature, soil conditions and cultural practices, this variation produces substantial overlapping of dimensions when comparing varieties and results in these dimensions having little use for comparing varieties.

IX. Propagation Methods

Asexual reproduction assures genetic stability and is used for increasing plant rootstock numbers to provide sufficient plants for commercial hop production. Sexual reproduction by plants of this variety is not possible because of its triploid genetic make up. The asexual propagation methodology utilizes 2 inch stem cuttings, which are treated with a rooting hormone and rooted in potting media in greenhouses. The rooted cuttings are grown in greenhouses under controlled conditions including without limitation control of temperature, humidity, light intensity, and daylength.

DETAILED DESCRIPTIVE INFORMATION

Following, is a detailed description of the botanical and analytical chemical characteristics of the new variety. The information for the botanical description was either collected or verified during the growing seasons of 1994 and 1995 in the growing area west of Toppenish, Wash. These botanical characteristics, and to a lesser degree the analytical chemical characteristics, are dependent on cultural practices and climatic conditions and can vary with location and season.

1. Parentage: A hop plant originating from a controlled cross pollination between and unpatented tetraploid USDA 21055 female hop plant with unpatented Haas male hop plant No. 833-53M.

2. Locality where grown and observed: Toppenish, Wash.
3. Dates of first and last harvest: Approximately September 10 and September 20 respectively, in Toppenish, Wash.
4. Plant characteristics:
   *Plant.*—Green vigorous, climbing vine.
   *Strip.*—Dark Green and purple.
   *Stipule direction.*—Down.
   *Plant shape.*—Columnar.
   *Leaf arrangement.*—Opposite.
   *Number of leaf lobes.*—3 to 7 (typically, 7, with 2 lobes being minor).
   *Leaf margin.*—Serrate to dentate.
   *Lateral length.*—37 inches average.
   *Internode length.*—9½ inches average.
5. Cone characteristics:
   *Bract tip shape.*—Cuspidate to mucronate.
   *Bract tip position.*—Loosely appressed.
   *Bracteole tip shape.*—Acute to narrowly rounded.
   *Compactness.*—Tight.
   *Shape.*—Ovoid to conic.
   *Cone length.*—1.75 inches average.
   *Cone tip shape.*—Pointed.
   *Stig.*—Thick.
   *Yield per acre.*—2600 to 3000 pounds average.
   *Maturity.*—Medium/Late.
6. Color characteristics: Fall color characteristics are unknown because the leaves are totally removed and destroyed during the harvesting procedure. Using the Colour Chart of The Royal Horticultural Society of London, Copyrighted 1966, the following color characteristics for H900322-4 have been determined.
   *Leaf upper surface.*—139A.
   *Leaf lower surface.*—138B.
   *Bine background.*—144A.
   *Bine stripe.*—144B, 59A.
   *Cone bracteole.*—141D.
   *Cone bract.* 141B.
7. Analytical Data of Cones*
   *% Alpha-acids (bale).*—16.0–18.0 (ASBC Spectrophotometric method).
   *% Beta-acids (bale).*—5.0 to 5.6 (ASBC Spectrophotometric method).
   *Alpha/Beta Ratio.*—2.8 to 3.2.
   *Cohumulone (% of alpha-acids).*—Average 44.0.
   *Colupulone (% of beta-acids).*—Average 66.0.
   *Storage characteristics.*—20.0% transformation after 6 months at 22°C (Based on USDA Hop Storage Index of baled hops) This rate of transformation is very comparable to that of the commerical varieties Galena and Nugget.
   *Total oils* (mls/100g).—Average 2.6.
   *Humulene (% of total oils).*—Average 19.0.
   *Caryophyllene (% of total oils).*—Average 8.6.
   *Humulene/caryophyllene ratio.*—Average 2.2.
   *Farnesene (% of total oils).*—Average 8.8.
   *Myrcene (% of total oils).*—Average 39.0.
   *Lupulin (% of total cone weight).*—Average 30.0.

*Analytical Data determined on hops with approximately 8% cone moisture.

8. Analytical data of Lupulin:
   *% Alpha-acids.*—Average 56.0.
   *% Beta-acids.*—Average 17.0.

Disease resistance: The variety H900322-4 is moderately susceptible to downy mildew noting that there is no known resistance to the disease in any variety of hop. H900322-4 is tolerant to strains of Verticillium wilt found and the viruses found in the USA growing areas, as well as to the major soil born pests including Phytophthera root rot.

10. Regional Adaptation: The H900322-4 variety appears to be adapted to both the drier and the more humid growing regions of the United States, specifically including the Yakima Valley of Washington State and the Willamette Valley of Oregon State.
11. Ploidy: The genetic make up of H900322-4 is tetraploid USDA 21055 × 833-53M (21055 × 63015M). The mother is tetraploid and the father is diploid, thus making H900322-4 a triploid plant. Because the variety is triploid, it is incapable of sexual reproduction. Reproduction can only be asexual.
12. Life expectancy: Life expectancy of this variety is not known, but presumed to be theoretically indefinite similar to other varieties of the same species.
13. Use: Flavoring for beers, stouts and ales.
14. Virus and propagation Status: H900322-4 rootstock has been virus tested and is virus-free. Propagatable plant material exists.

DISTINGUISHING CHARACTERISTICS

H900322-4 can be distinguished from all other USA commercial varieties by its high percentage of alpha-acids. No other commercial variety in the USA has alpha-acids of 16–18% routinely. Additionally, H900322-4 has a high amount of farnesene as a component in the essential oil (8.8% of total oil is farnesene). None of the USA high alpha-acids varieties has farnesene in the oil. Furthermore, H900322-4 has a higher cohumulone content (44.0%) of the alpha-acids than any of the USA high alpha-acids varieties.

The John I. Haas, Inc. patented variety H87311-3 (U.S. Plant Pat. No. 8,812) has alpha-acids contents of 16.5–18.5%. H900322-4 can be distinguished from H87311-3 by the farnesene content in the oil of H900322-4 (H87311-3 has none). Additionally, H900322-4 has cones with bracts that are darker green than the bracteoles. This produces the appearance of a striped cone. H87311-3 cones do not have this striped appearance because the bracts and bracteoles are nearly the same shade of green. Furthermore, H900322-4 produces a much fuller appearing plant on the string at harvest time due to the substantially higher yield of 2600–3000 pounds per acre compared to 1800–2200 for H87311-3.

I Claim:

1. A new variety of hop plant substantially as herein shown and described characterized by the unusually high percentage of alpha-acids in the cones and high cone yields per plant compared to all other commercially available varieties in the USA.

* * * * *